(12) United States Patent
Cirillo et al.

(10) Patent No.: US 6,242,453 B1
(45) Date of Patent: Jun. 5, 2001

(54) POLYCYCLO HETEROCYCLIC DERIVATIVES AS ANTIINFLAMMATORY AGENTS

(75) Inventors: Pier F. Cirillo, Woodbury; Eugene R. Hickey, Danbury, both of CT (US); John R. Regan, Larchmont, NY (US); Lin-Hua Zhang, New Fairfield, CT (US)

(73) Assignee: Boehringer Ingelheim Pharmaceuticals, Inc, Ridgefield, CT (US)

( * ) Notice: Subject to any disclaimer, the term of this patent is extended or adjusted under 35 U.S.C. 154(b) by 0 days.

(21) Appl. No.: 09/503,263

(22) Filed: Feb. 14, 2000

Related U.S. Application Data

(60) Provisional application No. 60/121,178, filed on Feb. 22, 1999.

(51) Int. Cl.[7] .......... C07D 487/04; A61K 31/38
(52) U.S. Cl. .......... 514/267; 544/250
(58) Field of Search .......... 544/250; 514/267

(56) References Cited

U.S. PATENT DOCUMENTS

| | | | |
|---|---|---|---|
| 4,105,766 | 8/1978 | Alexander | 424/251 |
| 4,303,660 * | 12/1981 | Bereuyi et al. | 424/251 |
| 4,435,567 | 3/1984 | Lugosi et al. | 544/165 |
| 5,162,360 | 11/1992 | Creswell et al. | 514/371 |
| 5,686,455 | 11/1997 | Adams et al. | 514/256 |
| 5,739,143 | 4/1998 | Adams et al. | 514/275 |
| 5,777,097 | 7/1998 | Lee et al. | 536/24.31 |
| 5,783,664 | 7/1998 | Lee et al. | 530/350 |
| 5,859,041 | 1/1999 | Liverton et al. | 514/396 |
| 5,869,043 | 2/1999 | McDonnell et al. | 424/94.1 |
| 5,871,934 | 2/1999 | Lee et al. | 435/7.1 |
| 5,916,760 | 6/1999 | Goeddel et al. | 435/15 |
| 5,948,885 | 9/1999 | Stein et al. | 530/324 |

FOREIGN PATENT DOCUMENTS

| | | |
|---|---|---|
| 293 352 | 8/1991 | (DE) . |
| 61228444 | 10/1986 | (EP) . |
| 0 272 866 | 6/1988 | (EP) . |
| 0 394 144 | 10/1990 | (EP) . |
| 0 418 071 | 3/1991 | (EP) . |
| 0692483 | 1/1996 | (EP) . |
| 0859054 | 8/1998 | (EP) . |
| 0922762 | 6/1999 | (EP) . |
| 0 955 293 | 10/1999 | (EP) . |
| 04039657 * | 2/1992 | (JP) . |
| 07043871 * | 2/1995 | (JP) . |
| 97/35856 | 10/1989 | (WO) . |
| 93/24458 | 9/1993 | (WO) . |
| 94/18170 | 8/1994 | (WO) . |
| 94/22866 | 10/1994 | (WO) . |
| 96/25157 | 8/1996 | (WO) . |
| 96/40143 | 12/1996 | (WO) . |
| 97/22704 | 6/1997 | (WO) . |
| 97/33883 | 9/1997 | (WO) . |
| 97/35855 | 10/1997 | (WO) . |
| 97/44467 | 11/1997 | (WO) . |
| 97/47618 | 12/1997 | (WO) . |
| 97/48697 | 12/1997 | (WO) . |
| 98/07425 | 2/1998 | (WO) . |
| 98/15618 | 4/1998 | (WO) . |
| 98/27098 | 6/1998 | (WO) . |
| 98/52558 | 11/1998 | (WO) . |
| 98/52559 | 11/1998 | (WO) . |
| 99/00357 | 1/1999 | (WO) . |
| 99/32106 | 7/1999 | (WO) . |
| 99/32110 | 7/1999 | (WO) . |
| 99/32111 | 7/1999 | (WO) . |
| 99/32455 | 7/1999 | (WO) . |
| 99/32463 | 7/1999 | (WO) . |
| 99/46244 | 9/1999 | (WO) . |
| 00/43384 | 7/2000 | (WO) . |

OTHER PUBLICATIONS

Jeffrey C. Boehm & Jerry L. Adams, New inhibitors of p38 kinase, Expert Opin.Ther. Patents (2000) 10(1):25–37.
Two novel structural classes of P38 kinase inhibitors; Exp. Opin. Ther. Patents (1999) 9(4):477–480.
SB 203580, Calbiochem—Cat. No. 559389—Revised May 30, 1997.
Jagadish C. Sircar, et al; Pyrazolo[5,1–b]quinazolin–9 ones: A New Series of Antiallergic Agents, J. Med. Chem. 1981, 24, 735–742.
Faherty et al., J. Immun., 148, pp. 766–771, 1992.*
Li et al., J. Immun., 148, pp. 788–794, 1992.*
Cooper et al., Ann. Reports Med. Chem. 27, pp. 209–218, 1992.*
Lamb, Ann. Reports Med. Chem. 31, p. 275, 1996.*
Black et al. Ann. Reports Med. Chem., 32, pp. 241–250, 1997.*

* cited by examiner

Primary Examiner—Richard L. Raymond
Assistant Examiner—Deepak R. Rao
(74) Attorney, Agent, or Firm—Robert P. Raymond; Anthony P. Bottino; Alan R. Stempel

(57) ABSTRACT

Disclosed are novel aromatic polycyclo heterocyclic compounds of the formula(I) wherein A, B, C, G, Ar, L, Q and X are described herein. The compounds are useful in pharmaceutical compositions for treating diseases or pathological conditions involving inflammation such as chronic inflammatory disease. Also disclosed are processes of making such compounds.

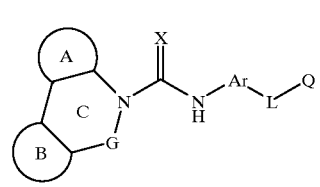

(I)

18 Claims, No Drawings

POLYCYCLO HETEROCYCLIC DERIVATIVES AS ANTIINFLAMMATORY AGENTS

RELATED APPLICATIONS

This application claims benefit to U.S. Provisional application Ser. No. 60/121,178, filed Feb. 22, 1999.

TECHNICAL FIELD OF THE INVENTION

This invention relates to heterocycles of formula (I):

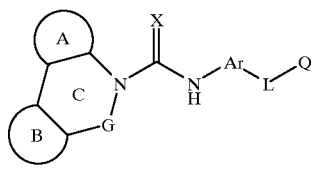

(I)

wherein A, B, C, G, X, Ar, L, and Q are defined below, which inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28–38). An important and accepted therapeutic approach for potential drug intervention in these diseases is the reduction of proinflammatory cytokines such as TNF (also referred to in its secreted cell-free form termed TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, *British J. Rheum.* 35: 334–342 and Stack, W. A., et al., 1997, *Lancet* 349: 521–524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitis shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24). Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A,* 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses* 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 -blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti- IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis.

Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dememtia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer us cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hema-* tol. 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFN α(Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN α has been shown to increase following a delayed type hypersensitivity reaction thus indicating a role for IFN γ in atopic dermatitis (Szepietowski, et al., 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ(Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al., 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 *Suppl* 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases.

U.S. Pat. No. 5,162,360 discloses N-substituted aryl-N'-heterocyclic substituted urea compounds which are described as being useful for treating hypercholesterolemia and atroclerosis.

The work cited above supports the principle that inhibition of cytokine production will be beneficial in the treatment of various disease states. Some protein therapeutics are in late development or have been approved for use in particular diseases. Protein therapeutics are costly to produce and have bioavailability and stability problems. Therefore a need exists for new small molecule inhibitors of cytokine production with optimized efficacy, pharmacokinetic and safety profiles.

BRIEF DESCRIPTION OF THE INVENTION

The work cited above supports the principle that inhibition of cytokine production will be beneficial in the treatment of various disease states.

It is therefore an object of the invention to provide novel compounds which inhibit the release of inflammatory cytokines such as interleukin-1 and tumor necrosis factor.

It is a further object of the invention to provide methods for treating diseases and pathological conditions involving inflammation such as chronic inflammatory disease, using the novel compounds of the invention.

It is yet a further object of the invention to provide processes of preparation of the above-mentioned novel compounds.

DETAILED DESCRIPTION OF THE INVENTION

The invention provides for compounds of the formula (I):

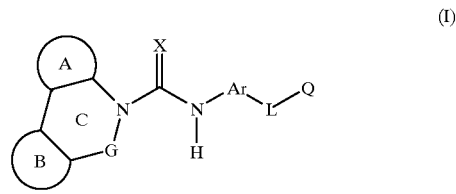

wherein:
A is pyrrole, pyrrolidine, pyrazole, imidazole, oxazole, thiazole, furan, or thiophene; wherein A may be optionally substituted by one or more $R_1$;
Ar is phenyl, naphthyl, quinoline, isoquinoline, tetrahydronaphthyl, tetrahydroquinoline, tetrahydroisoquinoline, benzimidazole, benzofuran, indanyl, indenyl, benzyl, benzo[1,3]dioxol-5-yl and indole each being optionally substituted with one to three $R_2$ or $R_3$ groups;
B is phenyl, naphthyl or pyridinyl, which may be substituted by one or more Y;
G is a methylene group $(CH_2)_n R_2 R_3$ wherein n is 0, 1, 2 or 3 such that the C ring is a 5, 6, 7 or 8 membered heterocyclic ring; or G is a >C=O group;

L is a chemical bond or a linking group selected from the group consisting of a $C_{1-10}$ saturated or unsaturated branched or unbranched carbon chain; wherein one or more methylene groups are optionally independently replaced by O, N or S; and wherein said linking group is optionally independently substituted with 0–2 oxo groups or one or more $C_{1-4}$ branched or unbranched alkyl further optionally substituted by one or more halogen atoms;

Q is selected from the group consisting of:
  a) phenyl, naphthyl, pyridine, pyrimidine, pyridazine, imidazole, benzimidazole, furan, thiophene, pyran, naphthyridine, oxazo[4,5-b]pyridine and imidazo[4,5-b]pyridine, which are optionally substituted with one to three groups consisting of halogen, $C_{1-6}$ alkyl, $C_{1-6}$ alkoxy, hydroxy, mono- or di-($C_{1-3}$ alkyl)amino, $C_{1-6}$alkyl-S(O)$_m$ and phenylamino wherein the phenyl ring is optionally substituted with one to two groups selected from the group consisting of halogen, $C_{1-6}$ alkyl and $C_{1-6}$ alkoxy;
  b) tetrahydropyran, tetrahydrofuran, 1,3-dioxolanone, 1,3-dioxanone, 1,4-dioxane, morpholine, thiomorpholine, thiomorpholine sulfoxide, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl;
  c) $C_{1-6}$ alkoxy, secondary or tertiary amine wherein the amino nitrogen is covalently bonded to groups selected from the group consisting of $C_{1-3}$ alkyl and $C_{1-5}$ alkoxyalkyl, phenylamino, wherein the phenyl ring is optionally substituted with one to two groups selected from the group consisting of halogen, $C_{1-6}$ alkoxy, hydroxy or mono- or di-($C_{1-3}$ alkyl)amino, $C_{1-6}$ alkyl-S(O)$_m$, phenyl-S(O)$_m$, wherein the phenyl ring is optionally substituted with one to two groups selected from the group consisting of halogen, $C_{1-6}$ alkoxy, hydroxy or mono- or di-($C_{1-3}$ alkyl)amino;
  d) hydrogen;

$R_1$ is selected from the group consisting of:
  (a) $C_{3-10}$ branched or unbranched alkyl, which may optionally be partially or fully halogenated, and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle, selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkyloxy which is optionally partially or fully halogenated, —C(O)NH$_2$ and di($C_{1-3}$)alkylaminocarbonyl;
  (b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl, which may optionally be partially or fully halogenated and which may optionally be substituted with one to three $C_{1-3}$ alkyl groups, or an analog of such cycloalkyl group wherein one to three ring methylene groups are replaced by groups independently selected from O, S, CHOH, >C=O, >C=S and NH;
  (c) $C_{3-10}$ branched alkenyl which may optionally be partially or fully halogenated, and which may optionally be substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl and bicycloheptanyl, hydroxy, cyano, $C_{1-3}$ alkyloxy which is optionally partially or fully halogenated, C(O)NH$_2$, mono- or di($C_{1-3}$)alkylaminocarbonyl;
  (d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group may optionally be substituted with one to three $C_{1-3}$ alkyl groups;
  (e) cyano; and,
  (f) methoxycarbonyl, ethoxycarbonyl and propoxycarbonyl;

$R_2$ and $R_3$ are each independently $C_{1-6}$ branched or unbranched alkyl which may optionally be partially or fully halogenated;

Y is halogen, hydroxy, cyano, $C_{1-3}$ alkyloxy which may optionally be partially or fully halogenated, phenyloxy, —C(O)NH$_2$, a mono- or di-($C_{1-3}$)alkyl aminocarbonyl, $C_{1-5}$ alky —C(O)—$C_{1-4}$ alkyl, amino-$C_{1-5}$ alkyl, mono- or di-($C_{1-3}$)alkylamino-$C_{1-5}$ alkyl, —S(O)$_2$NH$_2$, di-($C_{1-3}$)alkylamino-S(O)$_2$, $R_{12}$—$C_{1-5}$ alkyl, $R_{13}$—$C_{1-5}$alkoxy, $R_{14}$—C(O)—$C_{1-5}$alkyl, $R_{15}$—$C_{1-5}$ alkyl($R_{16}$)N;

m is 0, 1, 2 or 3;

X is O or S; and pharmaceutically acceptable derivatives or tautomers thereof.

Preferred are compounds of the formula (I) wherein Ar is phenyl or naphthyl.

More preferred are compounds of the formula (I) wherein Ar is phenyl or naphthyl and wherein:
  A is thiophene or pyrazole;
  L is chemical bond or $C_{1-6}$ saturated or unsaturated branched or unbranched carbon chain wherein one or more methylene groups are optionally independently replaced by O, N or S; and wherein said linking group is optionally independently substituted with 0–2 oxo groups or one or more $C_{1-4}$ branched or unbranched alkyl further optionally substituted by one or more halogen atoms;
  $R_1$ is $C_{1-4}$ alkyl branched or unbranched, cyclopropyl or cyclohexyl which may optionally be partially or fully halogenated and which may optionally be substituted with one to three $C_{1-3}$ alkyl groups.

Even more preferred are compounds of the formula (I) wherein A is pyrazole.

Yet even more preferred are compounds of the formula (I) wherein L is $C_{1-5}$ saturated carbon chain wherein one or more methylene groups are optionally independently replaced by O, N or S; and wherein said linking group is optionally substituted with 0–2 oxo groups and one or more $C_{1-4}$ branched or unbranched alkyl which may be substituted by one or more halogen atoms.

Further preferred embodiments of the compounds of the formula (I) are wherein L can be selected from the following:

L is propoxy, ethoxy or methoxy; preferably ethoxy;

L is methyl or propyl;

L is $C_{3-5}$ acetylene; or

L is methylamino.

Further, the aforementioned groups preferred for L can have, where possible, one or more methylene groups optionally independently replaced by O, N or S; and the L linking group can be optionally independently substituted with 0–2 oxo groups or one or more $C_{1-4}$ branched or unbranched alkyl, the $C_{1-4}$ alkyl may be further optionally substituted by one or more halogen atoms.

Yet still even more preferred compounds of the formula (I) are compounds wherein L is a chemical bond and Q is hydrogen or halogen.

Exemplary compounds of the invention include, but are not limited to:

2-tert-Butyl-5H-pyrazolo[1,5-a]quinazolin-4-carboxylic acid (2,3-dimethylphenyl)amide;

2-tert-Butyl-5H-pyrazolo[1,5-a]quinazolin-4-carboxylic acid (3-chloro-2,4-dimethoxyphenyl)amide;

2-tert-Butyl-5H-pyrazolo[1,5-a]quinazolin-4-carboxylic acid 2-methylbenzylamide;

2-tert-Butyl-5H-pyrazolo[1,5-a]quinazolin-4-carboxylic acid 4-chlorolphenylamid;

2-tert-Butyl-5H-pyrazolo[1,5-a]quinazolin-4-carboxylic acid indan-1-ylamide;

2-tert-Butyl-5H-pyrazolo[1,5-a]quinazolin-4-carboxylic acid indan-2-ylamide;

2-tert-Butyl-5H-pyrazolo[1,5-a]quinazolin-4-carboxylic acid indan-5-ylamide and 2-tert-Butyl-5H-pyrazolo[1,5-a]quinazolin-4-carboxylic acid benzo[1,3]dioxol-5-ylamide.

2-tert-Butyl-5H-pyrazolo[1,5-a]quinazolin-4-carboxylic acid [4-(2-morpholin-4-yl-ethoxy)-naphthalen-1-yl]amide;

2-tert-Butyl-5H-pyrazolo[1,5-a]quinazolin-4-carboxylic acid [4-(2-(-1-oxothiomorpholin-4-yl)naphthalen-1-yl]amide, 2-tert-Butyl-5H-pyrazolo[1,5-a]quinazolin-4-carboxylic acid [4-(2-morpholin-4-yl-ethoxy)-5,6,7,8-tetrahydro-naphthalen-1-yl]amide;

2-tert-Butyl-5,6-dihydro-1H-1,4-diaza-benzo[e]azulene-4-carboxylic acid [4-{2-morpholin-4-yl-ethoxy)-5,6,7,8-tetrahydro-naphthalen-1-yl]amide;

2-tert-Butyl-5,6-dihydro-1,4,10b-triaza-benzo[e]azulene-4-carboxylic acid [4-{2-morpholin-4-yl-ethoxy)-5,6,7,8-tetrahydro-naphthalen-1-yl]amide;

2-tert-Butyl-5,6-dihydro-1,4,10b-triaza-benzo[e]azulene-4-carboxylic acid [4-{2-morpholin-4-yl-ethoxy)-naphthalen-1-yl]amide;

2-tert-Butyl-5,6-dihydro-1-thia-4-aza-benzo[e]azulene-4-carboxylic acid [4-{2-morpholin-4-yl-ethoxy)-5,6,7,8-tetrahydro-naphthalen-1-yl]amide;

2-tert-Butyl-5,6-dihydro-1-thia-4-aza-benzo[e]azulene-4-carboxylic acid [4-{2-morpholin-4-yl-ethoxy)-naphthalen-1-yl]amide;

and pharmaceutically acceptable derivatives or tautomers thereof.

The following are preferred compounds of the invention:

2-tert-Butyl-5H-pyrazolo[1,5-a]quinazolin-4-carboxylic acid (2,3-dimethylphenyl)amide;

2-tert-Butyl-5H-pyrazolo[1,5-a]quinazolin-4-carboxylic acid (3-chloro-2,4-dimethoxyphenyl)amide;

2-tert-Butyl-5H-pyrazolo[1,5-a]quinazolin-4-carboxylic acid 2-methylbenzylamide;

2-tert-Butyl-5H-pyrazolo[1,5-a]quinazolin-4-carboxylic acid 4-chlorophenylamide;

2-tert-Butyl-5H-pyrazolo[1,5-a]quinazolin-4-carboxylic acid indan-1-ylamide;

2-tert-Butyl-5H-pyrazolo[1,5-a]quinazolin-4-carboxylic acid indan-2-ylamide;

2-tert-Butyl-5H-pyrazolo[1,5-a]quinazolin-4-carboxylic acid indan-5-ylamide;

2-tert-Butyl-5H-pyrazolo[1,5-a]quinazolin-4-carboxylic acid benzo[1,3]dioxol-5-ylamide and the pharmaceutically acceptable derivatives or tautomers thereof.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, pentoxy and hexoxy. All alkyl, alkenyl and alkynyl groups shall be understood as being branched or unbranched where structurally possible and unless otherwise specified.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula I can exist in more than one tautomeric form. The invention includes all such tautomers.

The invention includes pharmaceutically acceptable derivatives of compounds of formula I. A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—$(C_1-C_4$ alkyl$)_4^+$ salts.

In addition, the compounds of this invention include prodrugs of compounds of the formula (I). Prodrugs include those compounds that, upon simple chemical transformation, are modified to produce a compound of formula (1). Simple chemical transformations include hydrolysis, oxidation and reduction. Specifically, when a prodrug of this invention is administered to a patient, the prodrug may be transformed into a compound of formula (I), thereby imparting the desired pharmacological effect.

General Synthetic Methods

The Invention also provides for processes of making compounds of the formula (I). The compounds of the invention may be prepared by the methods illustrated in Schemes I and II below.

Reaction of phenylhydrazine (II) with a 3-substituted-3-oxo-propanenitrile gives a 5-amino-1-phenyl-3-substituted pyrazole (III). Pictet-Spengler reaction of III in acidic or neutral media with formaldehyde provides VI (Scheme I, Method A). Alternatively, a 3-substituted-3-oxopropanenitrile may be reacted with 2-hydrazinobenzoic acid (IV) giving lactam V, which may be reduced with a suitable reducing agent such as, for example, $LiAlH_4$ to provide VI (Method B).

A suitable reagent which provides an acyl with a leaving group to VI is reacted with VI. Such reagents include phosgene or phosgene equivalents, alkyl or aryl chloroformates and anhydrides, preferably phosgene or phosgene equivalents. For example, the reaction of VI with phosgene or a phosgene equivalent provides carbamoyl chloride VII. Reaction of VII with an appropriate amine gives the desired product I (Method C). Alternatively, reaction of VI with the appropriate isocyanate provides the desired product I (Method D). Compounds G—NCO or G—NH$_2$ in Scheme I may be commercially available, or may be prepared by methods known to those skilled in the art. If G is a precursor of Ar—L—Q, the desired final product (I) may be constructed by methods known to those skilled in the art.

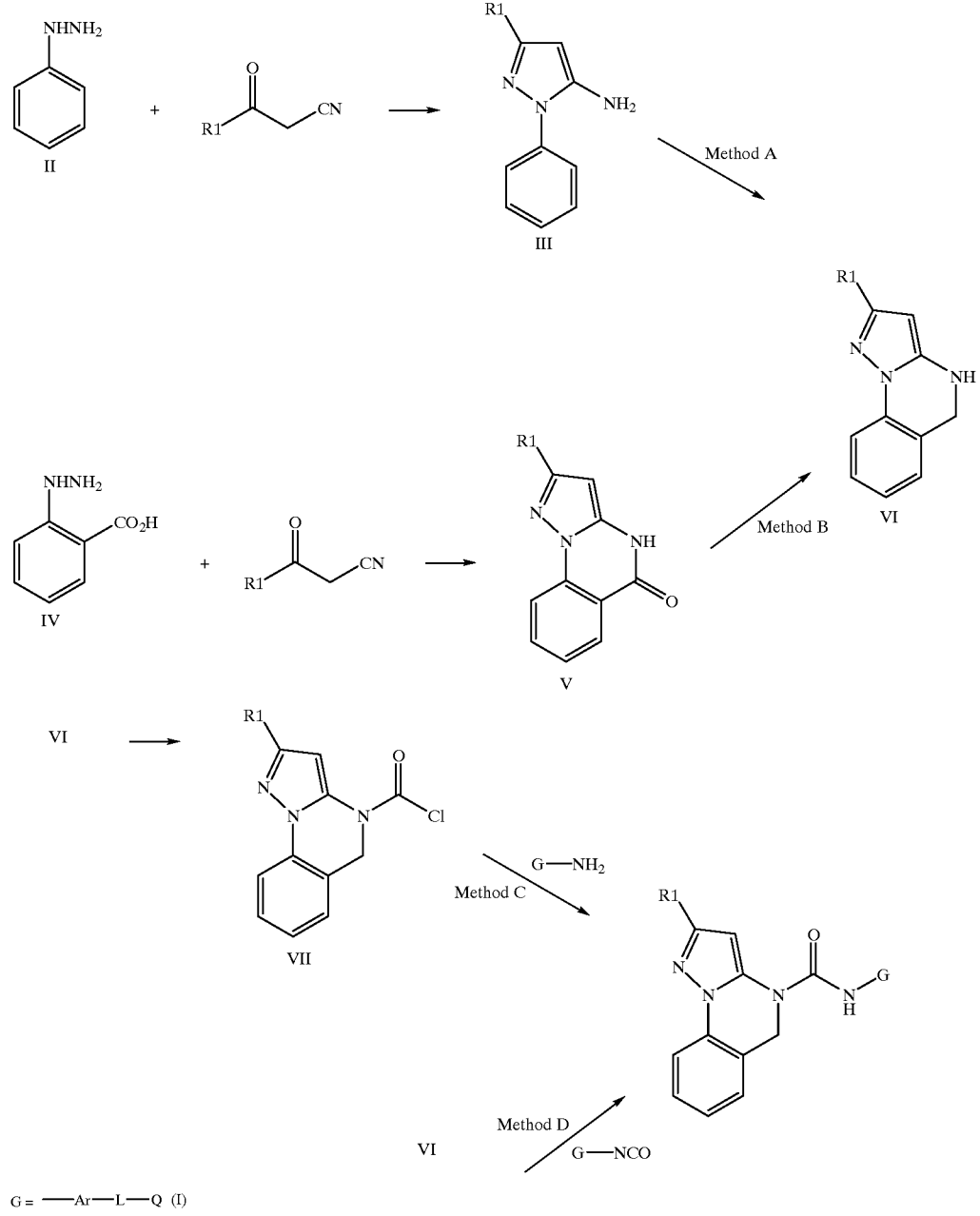

Scheme I

Compounds with A rings other than pyrazole may be similarly prepared as described in Scheme I, Merthod A, by using the substituted aminoheterocycle corresponding to III. Compounds with B rings other than phenyl, such as naphthyl or pyridal, can also be similarly prepared by using the appropriate aryl or heteroaryl hydrazine derivative instead of II. A general synthesis for the desired substituted aminothiophene is illustrated in Scheme II Scheme II

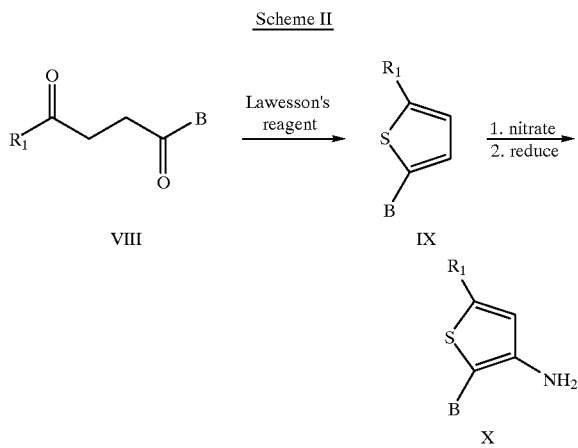

A mixture of substituted dione (VIII) and a sulfating reagent, such as Lawesson's reagent and phosphorous (V) sulfide, and preferrably Lawesson's reagent, is dissolved in a non-protic, anhydrous solvent, such as toluene, THF and dioxane. The preferred solvent is toluene. The mixture is heated at elevated temperatures and preferably at a solvent-refluxing temperature for 1–10 hr. The volatiles are removed and the residue is purified by silica gel chromatography using hexanes and ethyl acetate as eluent. The product-rich fractions are collected and the volatiles removed to provide the substituted thiophene IX.

A mixture of substituted thiophene IX is dissolved in a suitable solvent such as acetic anhydride or acetic acid. The preferred solvent is acetic anhydride. The mixture is cooled to about 0–30° C. and preferrably to about −10° C. A solution of concentrated nitric acid in a solvent such as acetic anhydride or acetic acid, with the preferred solvent being acetic anhydride and cooled to about 0–30° C. and preferrably to about −10° C., is added. The mixture is stirred between 10–120 min, poured onto ice and extracted with a non-protic solvent such as diethyl ether, chloroform, ethyl acetate or methylene chloride. The organic extracts are washed with aqueous alkali, dried with agents such as $MgSO_4$ and $Na_2SO_4$ and the volatiles removed. The residue is purified by silica gel chromatography using hexanes and ethyl acetate as eluents. The product -rich fractions are collected and the volatiles removed to provide the substituted 3-nitrothiophene. This is reduced by metals, such as iron, tin and zinc or catalytic hydrogenation. The preferred reduction occurs with iron in acetic acid at temperatures between 50–110° C. and preferrably at about 100° C. for 5–30 min. After cooling to room temperature the reaction is diluted with water, neutralized with alkali, such as sodium hydroxide, potassium hydroxide, potassium carbonate or sodium bicarbonate, and extracted with a non-protic solvent such as diethyl ether, ethyl acetate or methylene chloride. The organic extracts are dried with agents such as $MgSO_4$ and $Na_2SO_4$ and the volatiles removed to provide the desired aminothiophene X.

The synthesis of 2-amino-3,5-disubstituted thiophenes shown in Scheme III, is done in a fashion analogous to Knoll et al., J. Prakt. Chem., 1985, 327, 463. A mixture of substituted N-(3-aminothioacryloyl)-formamidine (XI) and substituted bromide (XII) in a protic solvent, such as methanol or ethanol, is heated, preferably at a reflux temperature, for 5–30 min and cooled below room temperature. The product thiophene-imine is filtered and dried. The thiophene-imine XIII is converted to the thiophene-amine (XIV) by treatment with aqueous acid.

Scheme III

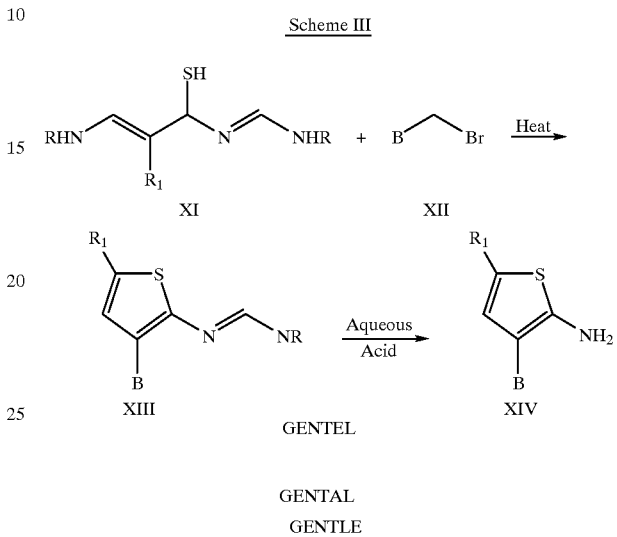

GENTEL

GENTAL

GENTLE

Scheme IV outlines a general scheme for desired aminofurans as described by Stevenson et al. (J. Am. Chem. Soc., 1937, 59, 2525). A ketoester (XV) is dissolved in a non-protic solvent, such as ether or THF, and treated with a strong base, such as sodium, sodium ethoxide or sodium hydride, and the anion is reacted with a bromomethyl ketone (XVI) at low temperatures, such as 20° C. After stirring the reaction until no starting material remains, it is poured onto cold water and extracted with a non-protic solvent. The combined extracts are dried with agents such as $MgSO_4$ or $Na_2SO_4$. The diketo-ester (XVII) may be carried forward without further purification or purified by distillation or silica gel chromatography. The diketo-ester in a protic solvent, such as ethanol, is heated in the presence of a mineral acid, such as sulfuric or hydrochloric, for 5–10 hr. and extracted with a non-protic solvent. The combined extracts are dried with agents such as $MgSO_4$ or $Na_2SO_4$. The furan-ester (XVIII) may be carried forward without further purification or purified by distillation or silica gel chromatography. The furan-ester in a protic solvent, such as ethanol, is treated with hydrazine hydrate and the mixture heated for 2–5 days. The hydrazide is isloated as above and treated with hot formic acid and the resulting substituted furan amine (XIX) purified by distillation or silica gel chromatography.

Scheme IV

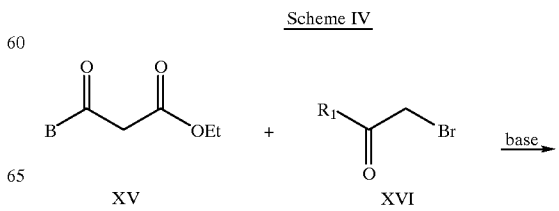

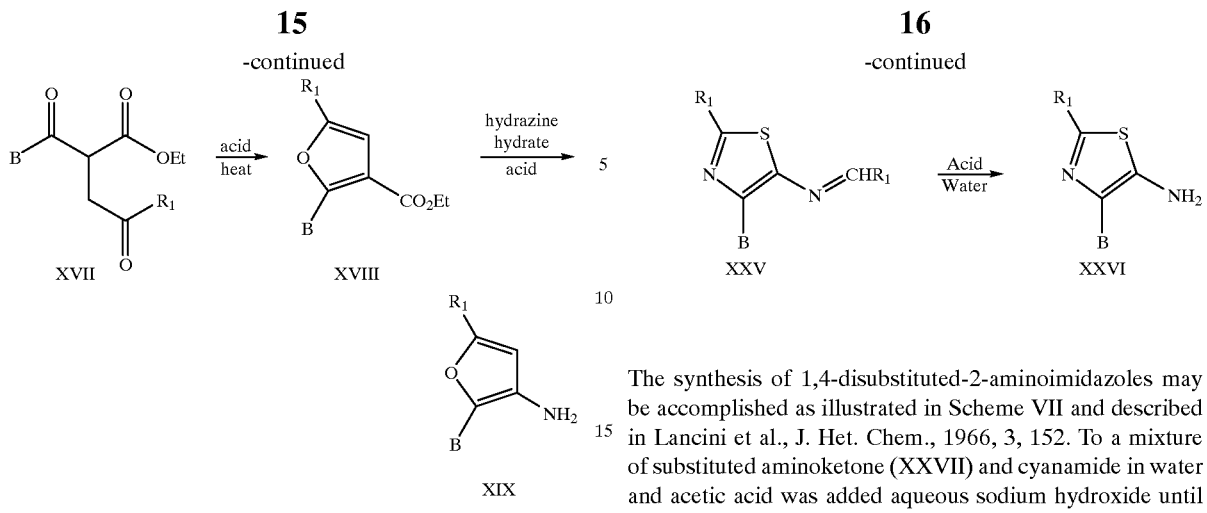

The synthesis of substituted 4-aminooxazoles may be achieved analogous to a procedure described by Lakhan et al. (J. Het. Chem., 1988, 25, 1413) and illustrated in Scheme V. A mixture of aroyl cyanide (XX), aldehyde (XXI) and anhydrous ammonium acetate in acetic acid is heated at about 100–111° C. for 3–6 hr, cooled to room temperature and quenched with water. Extraction by a non-protic solvent provides the product XXII which can be carried forward without further purification or purified by recrystallization or silica gel chromatography.

Scheme V

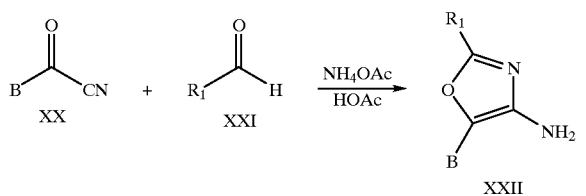

substituted 5-aminothiazoles (XXVI) may be prepared in a manner analogous to Gerwald et al., J. Prakt. Chem. 1973, 315, 539. As illustrated in Scheme VI, to a mixture of aminocyanide XXIII, aldehyde XXIV and sulfur in an anhydrous solvent, such as ethanol and methanol, is added dropwise a base, such as triethylamine. The mixture is heated at about 50° C. for 1–3 hr. The mixture is cooled and the excess sulfur removed. Acetic acid is added to neutralize the mixture and the solid collected. The imine XXV is treated with acid, such as hydrochloric and toluenesulfonic acid, in water and an organic solvent. After the starting material is consumed the reaction is worked up and the product XXXVI may be carried forward without further purification or purified by recrystallization or silica gel chromatography.

Scheme VI

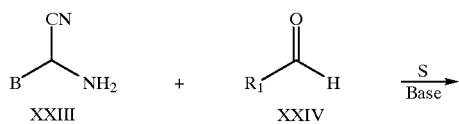

The synthesis of 1,4-disubstituted-2-aminoimidazoles may be accomplished as illustrated in Scheme VII and described in Lancini et al., J. Het. Chem., 1966, 3, 152. To a mixture of substituted aminoketone (XXVII) and cyanamide in water and acetic acid was added aqueous sodium hydroxide until a pH of about 4.5 is reached. The mixture is heated at about 50–90° C. for 1–5 hr, cooled and basicified with ammonium hydroxide. The product XXVIII is collected by filtration and dried.

Scheme VII

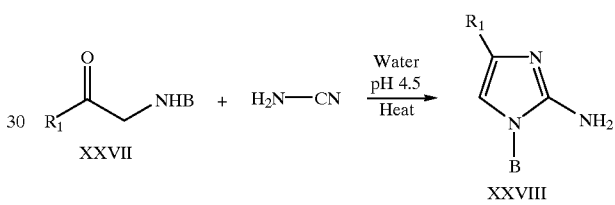

The synthesis of substituted 3-aminopyrroles (XXXII) may be achieved in a manner analogous to Aiello et al., J. Chem. Soc. Perkins Trans. I, 1981, 1. This is outlined in Scheme VIII. A mixture of diketone (XXIX) and amine (XXX) in acetic acid is heated at about 100–110° C. for 3–6 hr and worked up in the usual manner. The product (XXXI) in acetic acid is treated with a nitrating agent, such as nitric acid and potassium nitrate in concentrated sulfuric acid. The mixture is poured onto cold water and extracted with a non-protic solvent. The combined extracts are dried with agents such as $MgSO_4$ and $Na_2SO_4$. Removal of the volatiles provides the nitro-pyrrole which which may be carried forward without further purification or purified by recrystallization or silica gel chromatography. The nitro-pyrrole is reduced to the amine with iron in acetic acid or by catalytic hydrogenation using palladium on activated carbon. The substituted aminopyrrole (XXXII) may be carried forward without further purification or purified by recrystallization or silica gel chromatography.

Scheme VIII

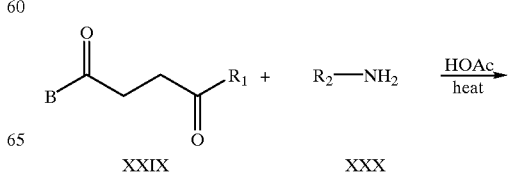

-continued

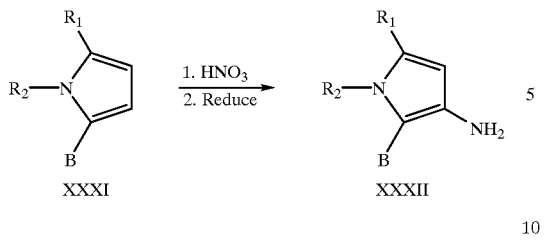

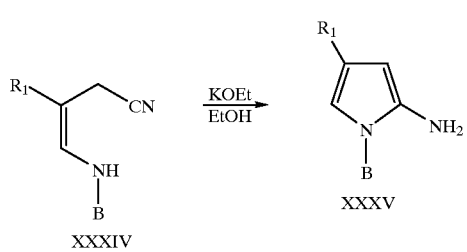

An isomeric aminopyrrole may be prepared as illustrated in Scheme IX. A mixture of amine XXIX and ketoaldehyde (XXX) in acetic acid is heated between 80–110° C. for 2–24 hr. The reaction is diluted with water and extracted with an organic solvent. The combined extracts are dried with agents such as $MgSO_4$ or $Na_2SO_4$ and the volatiles removed. The resulting pyrrole is treated with a nitrating agent and subsequently reduced to XXXI as described above. The product may be carried forward without further purification or purified by recrystallization or silica gel chromatography.

Compounds with expanded central rings (n=2 or 3) could be prepared as illustrated below in Scheme XI. Aminopyrazole intermediate XXXVI could be obtained by reaction of a 3-substituted-3-oxopropanenitrile with hydrazine by heating in a suitable solvent such as methanol. Reaction of a bromophenylacetyl chloride (XXXVII, n=1) or bromophenylpropionyl chloride (XXXVII, n=2) in a suitable solvent such as methylene chloride in the presence of a base such as $iPr_2NEt$ gives amides XXXVIII (n=1 or 2). These intermediates may be cyclized in the presence of a Pd catalyst and strong base such as potassium-t-butoxide to give lactams XXXIX (n=1 or 2). Reduction, for example with $LiAlH_4$, gives XL. This may be treated as described above in Methods C or D to give desired products with a 7-(XLI) or 8-membered (XLII) central ring.

Scheme IX

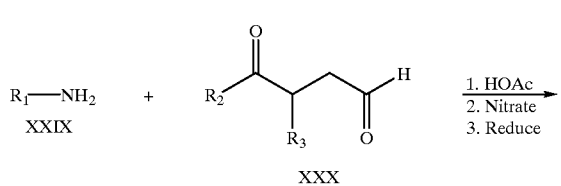

Scheme XI

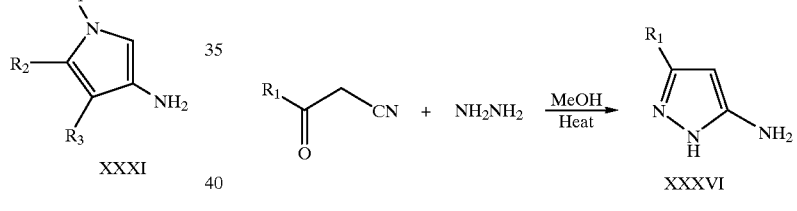

The synthesis of 1,4-disubstituted-2-aminopyrroles (XXXV) may be accomplished in a manner analogous to Brodrick et al. (J. Chem. Soc. Perkin Trans. I, 1975, 1910), and as illustrated in Scheme X. The potassium salt of formylnitrile XXXII in water is treated with amine XXXIII and acetic acid and the mixture heated at about 50–90° C. for 5–30 min. The aminonitrile XXXIV is collected by filtration upon cooling and then is stirred at room temperature with a base such as ethanolic potassium ethoxide for 2–5 hr and the volatiles removed. The residue is diluted with water and extracted with an organic solvent. The combined extracts are dried with an agent such as $MgSO_4$ or $Na_2SO_4$ and the volatiles removed. The product (XXXV) may be carried forward without further purification or purified by recrystallization or silica gel chromatography.

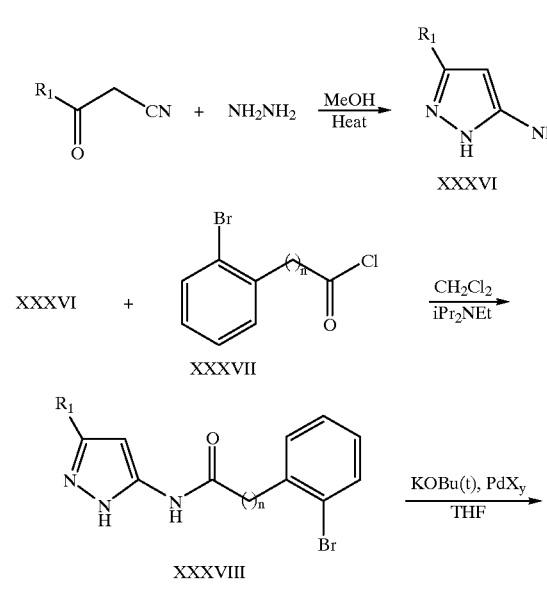

Scheme X

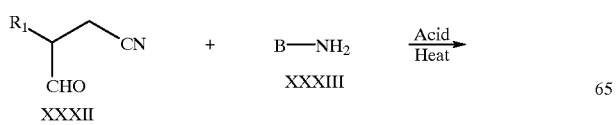

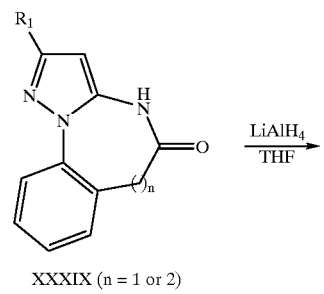

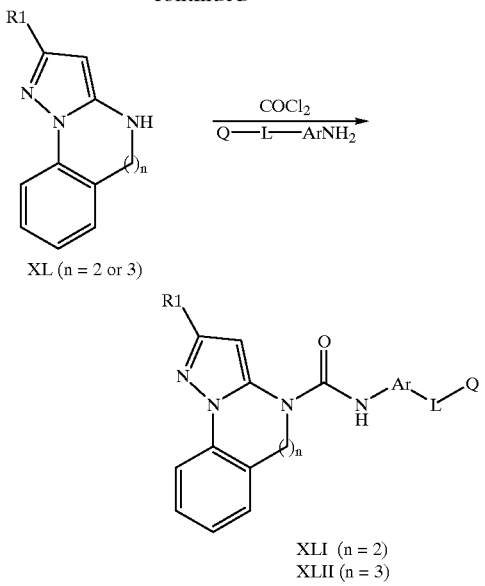

XL (n = 2 or 3)

XLI (n = 2)
XLII (n = 3)

Methods of Therapeutic Use

The compounds of the invention effectively block inflammatory cytokine production from cells. The inhibition of cytokine production is an attractive means for preventing and treating a variety of disorders associated with excess cytokine production, e.g., diseases and pathological conditions involving inflammation. Thus, the compounds of the invention are useful for the treatment of such conditions. These encompass chronic inflammatory diseases including, but not limited to, osteoarthritis, multiple sclerosis, Guillain-Barre syndrome, Crohn's disease, ulcerative colitis, psoriasis, graft versus host disease, systemic lupus erythematosus and insulin-dependent diabetes mellitus. The compounds of the invention can also be used to treat other disorders associated with the activity of elevated levels of proinflammatory cytokines such as responses to various infectious agents and a number of diseases of autoimmunity such as rheumatoid arthritis, toxic shock syndrome, diabetes and inflammatory bowel diseases unrelated to those listed above are discussed in the Background of the Invention.

In addition, the compounds of the invention being inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, the present novel compounds would be expected to exhibit efficacy against those disorders currently treated with COX inhibitors such as the familiar NSAIDs. These disorders include acute and chronic pain as well as symptoms of inflammation and cardiovascular disease.

As discussed in the Background of the Invention, IL-8 plays a role in the influx of neutrophils into sites of inflammation or injury. Therefore, in a yet further aspect of the invention, the compounds of the invention may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5 %, but more preferably at least about 20%, of a compound of formula (I) (w/w) or a combination thereof. The optimum percentage (w/w) of a compound of formula(I) may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

SYNTHETIC EXAMPLES

Example 1

2-tert-Butyl-5H-pyrazolo[1,5-a]quinazoline (VI, R= tert-butyl)

A solution of 2-hydrazinobenzoic acid HCl salt (19 g, 0.1 mol) and trimethylacetylacetonitrile (13 g, 0.1 mol) in ethanol (300 mL) was heated to reflux for 5 h. The solution was cooled to room temperature and stored overnight. The precipitated product was collected by filtration and washed with hexane to provide the desired cyclic amide product (V, $R_1$=tert-butyl), m.p. 249–250° C. $^1$H NMR (400 MHz, $CDCl_3$) δ11.50 (s, 1H), 8.29 (d, 1H), 8.15 (d, 1H), 7.80 (t, 1H), 7.38(t, 1H), 5.91 (s, 1H), 1.40(s, 9H). MS m/z (M$^+$) 227. Anal. Calcd for $C_{14}H_{15}N_3O$: C 69.71; H 6.22; N 17.63. Found: C 69.79; H 6.20; N 17.43.

A solution of lactam V from above (4.10 g, 17.0 mmol) in 51 mL of anhydrous THF was stirred under Ar at 0° C. and 51 mL of 1 M THF solution of $LiAlH_4$ was added. The solution was refluxed overnight under Ar. After cooling to room temperature, 3 mL of $H_2O$ and 200 mL of $CH_2Cl_2$ was added to the pot and stirred for 30 minutes. The mixture was poured into 50 mL of 10% NaOH solution and stirred for 10 minutes, then filtered through celite. The organic layer was washed with 20 mL of 10% citric acid solution, 50 mL of brine and dried over $K_2CO_3$. After solvent removal, the desired product (3.70 g, 95.9%) was collected as light yellow oil which then solidified: mp 51–3° C. $^1$H NMR (400 MHz, $CDCl_3$) δ7.77(d, 1H), 7.31(t, 1H), 7.09(m, 1H), 5.39(s, 1H), 4.38(s, 2H), 4.29(b, 1H), 1.37(s, 9H). MS m/z (M$^+$) 227. Anal. Calcd for $C_{14}H_{17}N_3$: C 74.01; H 7.49; N 18.50. Found: C 73.89; H 7.45; N 18.42.

Example 2

2-tert-Butyl-5H-pyrazolo[1,5-a]quinazoline-4-carboxylic acid 2-methylbenzylamide A solution of VI ($R_1$=tert-butyl) (100 mg, 0.44 mmol) and 2-methylbenzylisocynate (80 mg, 0.54 mmol) in 1.5 mL of anhydrous THF was stirred overnight at room temperature. The mixture was poured into 3 mL of EtOAc, and solids were removed by filtration. The filtrate was concentrated and chromatographed on silica gel with 10% EtOAc/Hexanes, to give the desired product (14 mg, 8.5%) as a white powder: mp 180–1° C.; $^1$H NMR (400 MHz, $CDCl_3$) δ7.80(d, 1H), 7.38(t, 1H), 7.30–7.10(m, 6H), 5.91(s, 1H), 5.70(b, 1H), 4.96(s, 2H), 4.50(d, 2H), 2.37(s, 3H), 1.35(s, 9H); MS m/z (M$^+$) 374. Anal. Calcd for $C_{23}H_{26}N_4O$: C, 73.80; H 6.95; N 14.97. Found: C 73.63; H 6.93; N 14.89.

Table 1 illustrates additional representative compounds of the invention, which were prepared by methods analogous to those described above.

TABLE 1

| Example | $R_1$ | Ar | L | Q | m.p. (° C.) |
|---|---|---|---|---|---|
| 3 | t-butyl | indan-2-yl | bond | H | 190–191 |
| 4 | t-butyl | benzo[1,3]dioxol-5-yl | bond | H | 193–194 |
| 5 | t-butyl | indan-5-yl | bond | H | 210–211 |

TABLE 1-continued

| Example | $R_1$ | Ar | L | Q | m.p. (° C.) |
|---|---|---|---|---|---|
| 6 | t-butyl | indan-1-yl | bond | H | 203–204 |
| 7 | t-butyl | Phenyl | bond | 3-Cl-2,4-diOMe | 206–207 |
| 8 | t-butyl | Phenyl | bond | 2,3-diMe | 173–174 |
| 9 | t-butyl | Phenyl | bond | 4-Cl | 188–189 |

Inhibition of TNFα Production in THP Cells

The inhibition of TNFα production can be measured in lipopolysaccharide stimulated THP cells. All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). The assay was performed under sterile conditions; only test compound preparation was nonsterile. Initial stock solutions were made in DMSO followed by dilution into RPMI 1640 2-fold higher than the desired final assay concentration. Confluent THP.1 cells ($2 \times 10^6$ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 μg/ml final; Sigma L-2630, from E. coli serotype 0111 .B4; stored as 1 mg/ml stock in endotoxin screened distilled $H_2O$ at −80° C.). Blanks (unstimulated) received $H_2O$ vehicle; final incubation volume was 250 μl. Overnight incubation (18–24 hr) proceeded as described above. The assay was terminated by centrifuging plates 5 min, room temperature, 1600 rpm (400 xg); supernatants were transferred to clean 96 well plates and stored -80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated IC50 value is the concentration of the test compound that caused a 50% decrease in TNFα production.

Preferred compounds have $IC_{50}$'s below 20 micromolar in this assay

What is claimed is:

1. A compound of the formula

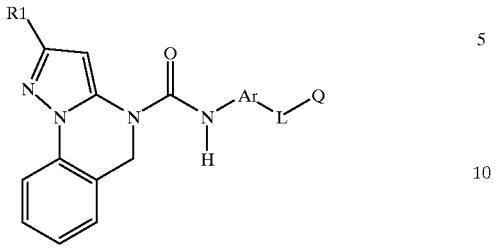

wherein:
Ar is phenyl, naphthyl, quinoline, isoquinoline, tetrahydronaphthyl, tetrahydroquinoline, tetrahydroisoquinoline, benzimidazole, benzofuran, indanyl, indenyl, benzyl, benzo[1,3]dioxol-5-yl and indole each being optionally substituted with one to three $R_2$ or $R_3$ groups;

L is a chemical bond or a linking group wherein said linking group is a $C_{1-10}$ saturated or unsaturated branched or unbranched carbon chain; wherein one or more methylene groups are optionally independently replaced by O, N or S; and wherein said linking group is optionally independently substituted with 0–oxo groups or one or more $C_{1-4}$ branched or unbranched alkyl further optionally substituted by one or more halogen atoms;

Q is selected from the group consisting of:
a) phenyl, naphthyl, pyridine, pyrimidine, pyridazine, imidazole, benzimidazole, furan, thiophene, pyran, naphthyridine, oxazo[4,5-b]pyridine and imidazo[4,5-b]pyridine, which are optionally substituted with one to three groups consisting of halogen, $C_{1-6}$ alkyl, $C_{1-6}$ alkoxy, hydroxy, mono- or di-($C_{1-3}$ alkyl)amino, $C_{1-6}$ alkyl-$S(O)_m$ and phenylamino wherein the phenyl ring is optionally substituted with one to two groups selected from the group consisting of halogen, $C_{1-6}$ alkyl and $C_{1-6}$ alkoxy;

b) tetrahydropyran, tetrahydrofuran, 1,3-dioxolanone, 1,3-dioxanone, 1,4-dioxane, morpholine, thiomorpholine, thiomorpholine sulfoxide, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of consisting of $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl;

c) $C_{1-6}$ alkoxy, secondary or tertiary amine wherein the amino nitrogen is covalently bonded to groups selected from the group consisting of $C_{1-3}$ alkyl and $C_{1-5}$alkoxyalkyl, phenylamino, wherein the phenyl ring is optionally substituted with one to two groups selected from the group consisting of halogen, $C_{1-6}$ alkoxy, hydroxy or mono- or di-($C_{1-3}$ alkyl)amino, $C_{1-6}$ alkyl-$S(O)_m$, phenyl-$S(O)_m$, wherein the phenyl ring is optionally substituted with one to two groups selected from the group consisting of halogen, $C_{1-6}$ alkoxy, hydroxy or mono- or di-($C_{1-3}$ alkyl)amino; or d) hydrogen;

$R_1$ is selected from the group consisting of:
a) $C_{3-10}$ branched or unbranched alkyl, which may optionally be partially or fully halogenated, and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle, selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkyloxy which is optionally partially or fully halogenated, —C(O)NH$_2$ and di($C_{1-3}$)alkylaminocarbonyl;

b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl, which may optionally be partially or fully halogenated and which may optionally be substituted with one to three $C_{1-3}$ alkyl groups, or an analog of such cycloalkyl group wherein one to three ring methylene groups are replaced by groups independently selected from O, S, CHOH, >C=O, >C=S and NH;

c) $C_{3-10}$ branched alkenyl which may optionally be partially or fully halogenated, and which may optionally be substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl and bicycloheptanyl, hydroxy, cyano, $C_{1-3}$ alkyloxy which is optionally partially or fully halogenated, C(O)NH$_2$, mono- or di($C_{1-3}$)alkylaminocarbonyl;

d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group may optionally be substituted with one to three $C_{1-3}$ alkyl groups;

e) cyano; and, f) methoxycarbonyl, ethoxycarbonyl and propoxycarbonyl;

$R_2$ and $R_3$ are each independently a $C_{1-6}$ branched or unbranched alkyl which may optionally be partially or fully halogenated;

m is 0, 1, 2 or 3;

X is O or S; and pharmaceutically acceptable salts or tautomers thereof.

2. A compound according to claim 1 wherein Ar is phenyl or naphthyl.

3. A compound according to claim 2 wherein:

L is chemical bond or $C_{1-6}$ saturated or unsaturated branched or unbranched carbon chain wherein one or more methylene groups are optionally independently replaced by O, N or S; and wherein said linking group is optionally independently substituted with 0–2 oxo groups or one or more $C_{1-4}$ branched or unbranched alkyl further optionally substituted by one or more halogen atoms;

$R_1$ is $C_{1-4}$alkyl branched or unbranched, cyclopropyl or cyclohexyl which may optionally be partially or fully halogenated and which may optionally be substituted with one to three $C_{1-3}$ alkyl groups.

4. A compound according to claim 3 wherein L is $C_{1-5}$ saturated carbon chain wherein one or more methylene groups are optionally independently replaced by O, N or S; and
wherein said linking group is optionally independently substituted with 0–2 oxo groups or one or more $C_{1-4}$ branched or unbranched alkyl further optionally substituted by one or more halogen atoms.

5. A compound according to claim 4 wherein L is propoxy, ethoxy or methoxy.

6. A compound according to claim 5 wherein L is ethoxy.

7. A compound according to claim 4 wherein L is methyl or propyl.

8. A compound according to claim 3 wherein
L is $C_{3-5}$ acetylene
wherein one or more methylene groups are optionally independently replaced by O, N or S; and
wherein said linking group is optionally substituted with 0–2 oxo groups and one or more $C_{1-4}$ branched or unbranched alkyl which may be substituted by one or more halogen atoms.

9. A compound according to claim 4 wherein L is methylamino.

10. A compound according to claim 3 wherein L is a chemical bond and Q is hydrogen.

11. A compound selected from the group consisting of:
2-tert-Butyl-5H-pyrazolo[1,5-a]quinazolin-4-carboxylic acid (2,3-dimethylphenyl)amide;
2-tert-Butyl-5H-pyrazolo[1,5-a]quinazolin-4-carboxylic acid (3-chloro-2,4-dimethoxyphenyl)amide;
2-tert-Butyl-5H-pyrazolo[1,5-a]quinazolin-4-carboxylic acid 2-methylbenzylamide;
2-tert-Butyl-5H-pyrazolo[1,5-a]quinazolin-4-carboxylic acid 4-chlorolphenylamide,
2-tert-Butyl-5H-pyrazolo[1,5-a]quinazolin-4-carboxylic acid indan-1-ylamide;
2-tert-Butyl-5H-pyrazolo[1,5-a]quinazolin-4-carboxylic acid indan-2-ylamide;
2-tert-Butyl-5H-pyrazolo[1,5-a]quinazolin-4-carboxylic acid indan-5-ylamide and
2-tert-Butyl-5H-pyrazolo[1,5-a]quinazolin-4-carboxylic acid benzo[1,3]dioxol-5-ylamide,
and the pharmaceutically acceptable derivatives or tautomers thereof.

12. A process of making a compound of the formula

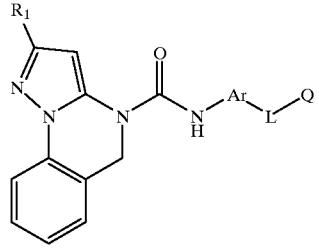

wherein Ar, L, $R_1$ and Q are defined as in claim 1, said process comprising:

a) reacting a 2-hydrazinobenzoic acid (IV) with a 3-substituted-3-oxopropanenitrile to form a tricyclo fused lactam (V):

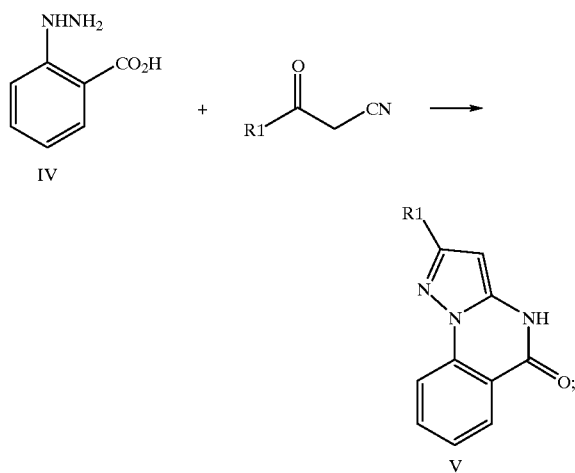

b) reducing compound (V) of step a) with a suitable reducing agent to form a pyrazolo quinazolin (VI):

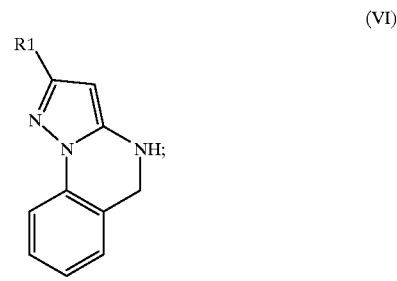

c) reacting the compound (VI) of step b) with a suitable phosgene compound to produce a carbamyl chloride compound of the formula (VII):

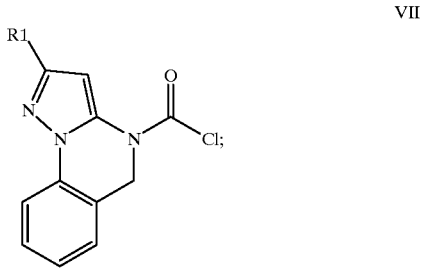

d) coupling the compound (VII) produced in step c) with a compound

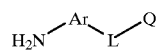

wherein Ar, L and Q are defined as in claim 1;

to form a compound of the formula:

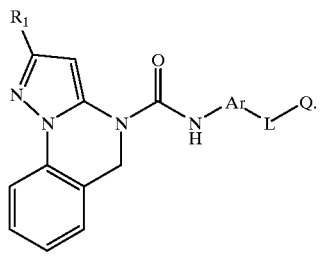

13. A pharmaceutical composition comprising a pharmaceutically effective amount of a compound according to claim 1.

14. A method of treating an inflammatory disease selected from the group consisting of osteoarthritis, multiple sclerosis, Guillain-Barre syndrome, Crohn's disease, ulcerative colitis, psoriasis, graft versus host disease, systemic lupus erythematosus and insulin-dependent diabetes mellitus, which comprises administering to a patient in need of such treatment a therapeutically effective amount of a compound according to claim 1.

15. A method of treating an autoimmune disease selected from the group consisting of rheumatoid arthritis, toxic shock syndrome, diabetes and inflammatory bowel disease which comprises administering to a patient in need of such treatment a therapeutically effective amount of a compound according to claim 1.

16. A method of treating acute or chronic pain which comprises administering to a patient in need of such treatment a therapeutically effective amount of a compound according to claim 1.

17. A method of treating a disease mediated directly or indirectly by TNFα wherein said disease is selected from the group consisting of osteoporosis and Alzheimer's disease said method comprises administering to a patient in need of such treatment a therapeutically effective amount of a compound according to claim 1.

18. A method of treating a neutrophil-mediated disease selected from the group consisting of stroke, myocardial infarction, thermal injury, adult respiratory distress syndrome (ARDS), multiple organ injury secondary to trauma, acute glomerulonephritis, dermatoses with acute inflammatory components, acute purulent meningitis and necrotizing entrerocolitis, said method comprises administering to a patient in need of such treatment a therapeutically effective amount of a compound according to claim 1.

* * * * *